US009146192B2

(12) United States Patent
Some et al.

(10) Patent No.: US 9,146,192 B2
(45) Date of Patent: Sep. 29, 2015

(54) INTEGRATED LIGHT SCATTERING AND ULTRAVIOLET ABSORPTION MEASUREMENT SYSTEM

(71) Applicant: Wyatt Technology Corporation, Santa Barbara, CA (US)

(72) Inventors: Daniel I. Some, Santa Barbara, CA (US); David N. Villalpando, Lompoc, CA (US)

(73) Assignee: WYATT TECHNOLOGY CORPORATION, Santa Barbara, CA (US)

( * ) Notice: Subject to any disclaimer, the term of this patent is extended or adjusted under 35 U.S.C. 154(b) by 0 days.

(21) Appl. No.: 13/896,120

(22) Filed: May 16, 2013

(65) Prior Publication Data
US 2013/0308121 A1 Nov. 21, 2013

Related U.S. Application Data

(60) Provisional application No. 61/648,541, filed on May 17, 2012.

(51) Int. Cl.
*G01N 21/47* (2006.01)
*G01N 21/33* (2006.01)
*G01N 21/53* (2006.01)

(52) U.S. Cl.
CPC ............. *G01N 21/47* (2013.01); *G01N 21/33* (2013.01); *G01N 21/532* (2013.01)

(58) Field of Classification Search
USPC ........... 356/335–343, 317, 319, 329, 73, 246, 356/432, 436, 437; 436/45, 70, 86
See application file for complete search history.

(56) References Cited

U.S. PATENT DOCUMENTS

| | | | | |
|---|---|---|---|---|
| 3,089,382 A | * | 5/1963 | Hecht | 356/410 |
| 4,616,927 A | | 10/1986 | Phillips et al. | |
| 4,907,884 A | | 3/1990 | Phillips et al. | |
| 5,168,326 A | * | 12/1992 | Tokieda et al. | 356/368 |
| 5,194,921 A | * | 3/1993 | Tambo et al. | 356/432 |
| 5,250,186 A | * | 10/1993 | Dollinger et al. | 210/656 |

(Continued)

OTHER PUBLICATIONS

Wyatt Technology Corporation, Dawn Heleos II promotional literature, 2007, Wyatt Technology Corporation, Goleta, USA.

(Continued)

*Primary Examiner* — Sang Nguyen
(74) *Attorney, Agent, or Firm* — David N. Villalpando; Philip J. Wyatt

(57) ABSTRACT

Various embodiments of integrated measurement cell systems for the simultaneous or near simultaneous measurement of light scattering and UV absorption measurements, and methods of their use, are disclosed. In the flow cell implementations, the height of the measurement cell is traversed by the UV beam multiple times by beam directing optics, allowing thereby, the accurate determination of concentration present in the integrated flow cell and allowing the user to select the desired sensitivity which is proportional to the number of passes the beam makes through the cell. Batch implementations also allow for near simultaneous measurement of light scattering and UV absorption within the cuvette. These embodiments aid in the reduction or elimination of errors due to interdetector band broadening while also decreasing the amount of sample required and improving design flexibility of integrated measurement systems.

15 Claims, 10 Drawing Sheets a) Side view b) Front view c) Front view

(56) References Cited

U.S. PATENT DOCUMENTS

| | | | |
|---|---|---|---|
| 5,305,071 A * | 4/1994 | Wyatt | 356/73 |
| 6,519,033 B1 * | 2/2003 | Quist et al. | 356/337 |
| 6,525,325 B1 * | 2/2003 | Andrews et al. | 250/461.1 |
| 6,930,769 B1 * | 8/2005 | Davis et al. | 356/213 |
| 7,294,513 B2 * | 11/2007 | Wyatt | 436/45 |
| 7,386,427 B2 | 6/2008 | Trainoff | |
| 7,630,076 B2 | 12/2009 | Kalonia et al. | |
| 7,911,594 B2 | 3/2011 | Trainoff | |
| 2003/0025909 A1 * | 2/2003 | Hallstadius | 356/436 |
| 2007/0178013 A1 * | 8/2007 | Kalonia et al. | 422/82.05 |
| 2008/0212073 A1 * | 9/2008 | Ehring | 356/51 |
| 2009/0219528 A1 * | 9/2009 | Chamberlin et al. | 356/319 |
| 2010/0314535 A1 * | 12/2010 | Zhang et al. | 250/252.1 |
| 2012/0202278 A1 * | 8/2012 | Wagner et al. | 435/288.7 |

OTHER PUBLICATIONS

Wyatt Technology Corporation, Optilab T-rEX promotional literature, 2010, Wyatt Technology Corporation, Goleta, USA.

Agilent Technologies, Agilent 1260 Infinity Multiple Wavelength Detector, 2010, Agilent Technologies, Inc., USA.

* cited by examiner

PRIOR ART

FIGURE 1

PRIOR ART

FIGURE 4 a) Front view b) Front view c) Side view

Side view

FIGURE 7

Top view

INTEGRATED LIGHT SCATTERING AND ULTRAVIOLET ABSORPTION MEASUREMENT SYSTEM

BACKGROUND

Multi-angle light scattering (MALS) is often used to characterize molar mass and size of macromolecules in solution by measuring the light scattering properties of the solution as it passes through a flow cell. MALS may also be used to characterize macromolecular interactions in solution by measuring the light scattering properties from a series of sample concentrations or compositions which are injected into the flow cell, usually with a stopped-flow period following the injection. The analysis of MALS data to determine molar mass and interaction properties generally requires knowledge of the concentration of the macromolecule in the MALS cell. The concentration of molecules in solution may be determined by measurement of the sample solution with a concentration detector such as a ultra-violet/visible light absorption (UV/Vis) spectrophotometer or differential refractometer. Typically the concentration detector comprises a flow cell separate from the MALS cell, often contained in an entirely different enclosure or instrument, the two cells being connected by capillary tubing so that sample passes from one cell to the other sequentially. Alternatively, the measurement may be made simultaneously by both instruments by splitting the flow between them with the correct split flow ratio.

Simultaneous, split-flow measurement may introduce certain systematic errors in data interpretation since the concentration in the MALS cell may not be identical to that in the concentration detector cell. This can be due, in part, to inaccuracy of the initial split flow ratio between the two cells, as well as the flow ratio changing in the course of a measurement due to changes in solution viscosity or in capillary dimensions as a result of thermal expansion or clogging. The systematic errors may be partially overcome by increasing the volume of sample delivered to the detectors, but this is undesirable as many samples of interest are not available in sufficient quantity.

In the case of sequential flow, an error in concentration measurement may occur due to the finite mixing volumes of the cells and intermediate capillary tubing, often referred to as band broadening. As each fraction passes through a detection device, it produces a signal often referred to as a "band" or "peak." Because of dispersion and mixing effects, these bands are broadened somewhat each time the sample passes through a different device. Consider a sample comprised of a low concentration aliquot of a monodisperse protein. In this event, the excess Rayleigh ratio is directly proportional to the molar mass and the concentration. The light scattering signal and the concentration signal should be of identical shape and would overlay perfectly were the two responses normalized to have the same areas. However, as the sample passes from the MALS detector and enters the concentration detector, it passes through intermediate regions and connections that contribute to the dispersion and mixing of the sample. Band broadening and mathematical methods for correcting its effects are described in U.S. Pat. No. 7,386,427, "Method for correcting the effects of interdetector band broadening," issued on Jun. 10, 2008, by S. Trainoff, and U.S. Pat. No. 7,911,594, "Method to derive physical properties of a sample after correcting the effects of interdetector band broadening," issued on Mar. 22, 2011, also by S. Trainoff, both of which are incorporated herein by reference.

The structure of the flow cells can add significantly to the measurement capabilities of the respective instruments. For example, the MALS cell discussed in U.S. Pat. No. 4,616,927, "Sample cell for light scattering measurements," by Steven D. Phillips, et. al. issued Oct. 14, 1986, and U.S. Pat. No. 4,907,884, "Sample cell monitoring system," by P. Wyatt et. al., issued Mar. 13, 1990, both patents herein incorporated by reference, disclose the use of a cylindrical flow cell through which has been drilled a bore. The sample passes through the bore, the cylindrical cell acts as a lateral lens, and the liquid glass interfaces are far removed from the scattering volume, thereby enabling the examination of the light scattered by the solution at virtually all scattering angles without introducing significant background artifacts from the cell itself.

The sensitivity of measurements made within a UV/Vis cell is greatly affected by the path length being traversed by the UV light source. The Beer-Lambert Law states:

$$A = \epsilon c l \quad (1)$$

where A is the absorbance, $\epsilon$ is the molar absorption coefficient, c is the concentration of the sample and l is the path length traversed by the UV beam through the sample. If, then, A is measured by the spectrophotometer, and the $\epsilon$ and l are known, the concentration c may be determined. Further, the longer the path length, l, the greater the sensitivity of the measurement of the concentration is likely to be.

It is an objective of the present invention to minimize band broadening between MALS and UV measurements while improving the overall sensitivity of the concentration detection by enabling a variable UV beam path length. It is a further objective of the invention to facilitate the integration of both UV/Vis absorption and MALS detection within a single analytical instrument as well as to enable such a dual measurement system, via a drop-in/modular modification, into an existing MALS-only detection instrument without need for extensive instrument alteration or re-design.

BRIEF DESCRIPTION OF THE INVENTION

A novel integrated flow cell system for the simultaneous measurement of MALS and UV concentration measurements is disclosed. In one embodiment, the cell is traversed several times by the UV beam, allowing, thereby, the accurate determination of concentration present in the integrated flow cell. The cell aids in the elimination of errors due to interdetector band broadening while also decreasing the amount of sample required. It further aids in the analysis of data acquired from the detection systems, as no correction is required to address band broadening issues.

BRIEF DESCRIPTION OF THE DRAWINGS

FIG. 5a is an example where optical elements may be placed into recesses in the cell structure; FIG. 5b shows a possible implementation with alignment and retaining elements which hold the optical elements in proper position with respect to a cell manifold and the cell structure; and FIG. 5c exhibits an embodiment wherein the bottom optical element is may be used in conjunction with a variety of interchangeable top optical elements.

DETAILED DESCRIPTION OF THE INVENTION

Figure 1:
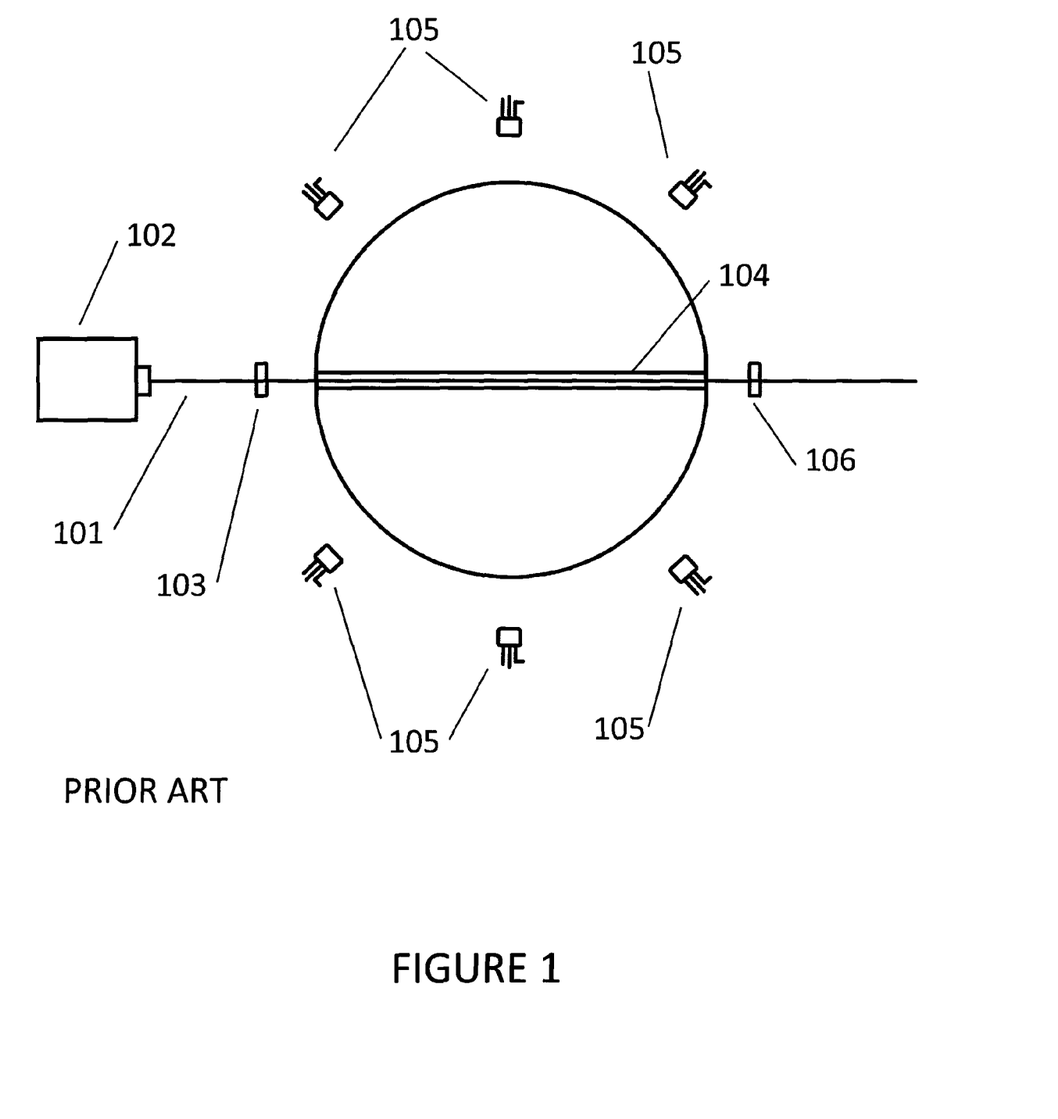
FIG. 1 illustrates a conventional multi angle light scattering detector cell similar to that disclosed by Phillips.

In a conventional right cylindrical MALS measurement cell, such as that described by Phillips, and shown in FIG. 1, a beam of light 101, generally emitted by a laser 102 passes through a window 103 and into a channel 104 bored through a diameter of the measurement flow cell. Light is scattered from the sample solution contained therein and is detected by a plurality of detectors 105 located radially in a plane about the scattering volume, which is an area defined by the intersection of the beam 101 with the field of view of the detectors 105, generally near the center of the cell. Non-scattered light exits through the exit window 106.

Figure 2:
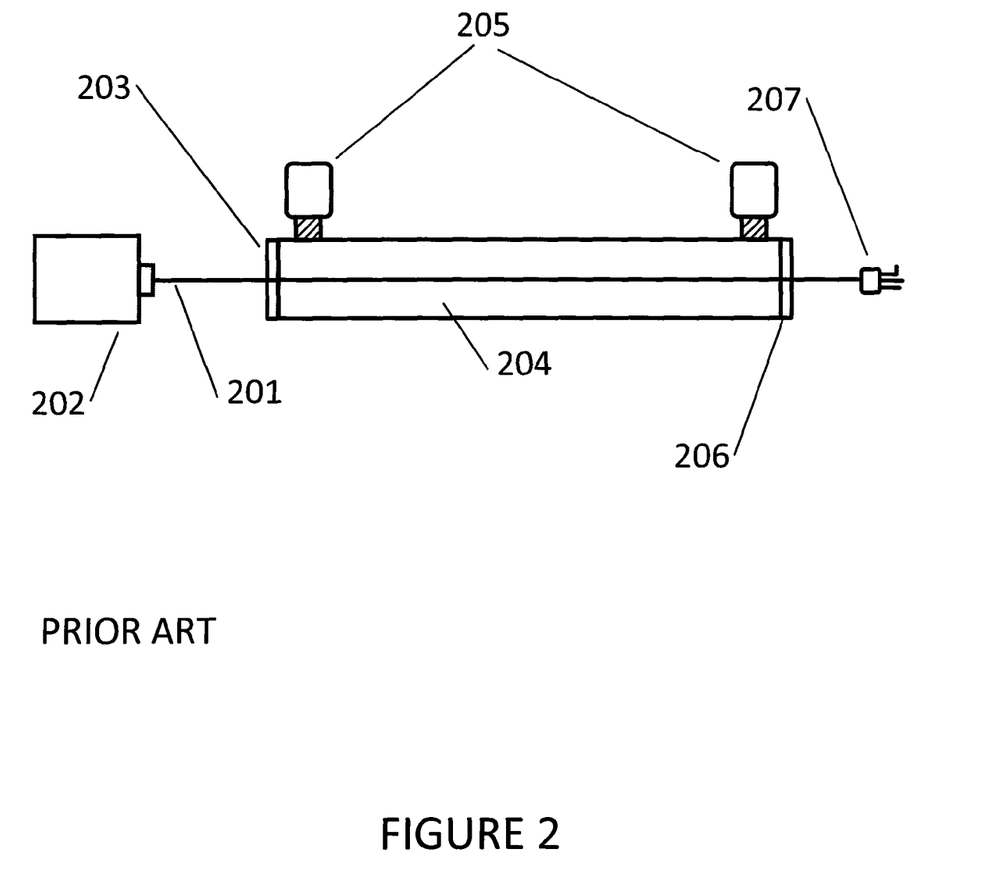
FIG. 2 illustrates a conventional UV/vis measurement cell system.

A conventional UV/vis absorbance detector often utilizes varying light sources allowing for operation at variable wavelengths, sometimes in the visible spectrum, such as that emanated by a tungsten lamp, or in the ultraviolet spectrum, such as a beam emitted from a deuterium source. It should be noted that the beam used in a UV/vis detection system can operate, as discussed above, either in the visible or ultraviolet range of electromagnetic radiation. For the purposes of this disclosure, the beam utilized by the UV/vis system will generally be referred to as the UV beam regardless of whether or not the wavelength is within the UV or visible light spectrum. Further the term UV/vis measurement system will be referred to as the UV detector and or system. A UV flow cell system, such as that shown in FIG. 2, directs a beam 201 from a UV source 202 through a window 203 and into a chamber 204 which contains the sample which is to be measured. Flow inlet and outlet ports 205 may be present to allow the sample to flow in and out of the measurement chamber where the beam is partly absorbed by the sample. The non-absorbed beam then exits the chamber via the exit window 206 and falls upon a detector 207 which is used to measure the amount of non-absorbed light. The longer the path length through which the beam travels is, the more sensitive the measurement. The walls of the chamber 204 may be constructed of any material capable of having windows attached thereto and able to be sealed for fluid flow, if it is operating as a flow cell. If the cell is operating in non-flow or "batch mode," the cell may be a simple cuvette, open or closed from above, which can be supplied with an aliquot of sample, and which has windows transparent to UV radiation through which the beam may pass.

For the measurement of certain macromolecules such as proteins by MALS and concentration detection, the determination of concentration by means of UV absorption is often the preferred technique. The errors associated with band broadening between MALS and UV cells may be overcome by unifying the MALS and concentration measurement in a single flow cell. The advantages of such a cell have been described Kalonia, Harminder and Vikas in U.S. Pat. No. 7,630,076, "Dual-detector systems with methods having utility in biomolecular measurements," issued Dec. 8, 2009. Prior attempts to incorporate both MALS and UV absorption into a single cell, including that by Kalonia and Bajaj, generally resulted in sub-optimal designs that make compromises on several fronts. In terms of MALS, the Kalonia design at best incorporates only two scattering angles, in contrast to the more advanced MALS detectors incorporating up to 18 angles such as the DAWN® systems produced by Wyatt Technology Corporation, Santa Barbara, Calif. No less significantly, this cell geometry presents glass-liquid and glass-air interfaces close to the volume viewed by the detector and hence permits stray light generated at those interfaces to reach the MALS detectors, introducing significant error in the data. In terms of UV absorption, the short UV path length of approximately 3 mm results in insufficient absorption to make measurements at low sample concentrations.

Another consideration regarding the previous attempts at an integrated sample cell is in terms of sample consumption. For example, the geometry of the Kalonia cell body and its inlet and outlet orifices create an effective mixing volume which is large relative to the physical volume, resulting in unnecessarily large sample volume requirements. Reduction of the cell volume would produce a corresponding improvement in sample requirement but degrade further the optical performance by reducing the UV absorption path as well as moving the interfaces closer together. Conversely, optical performance may be improved at the cost of increased sample volumes.

The problem of stray light and multiple detection angles can be resolved by means of an elongated flow path wherein the glass-air and glass-fluid interfaces directly impinged by the laser beam are far from the detection volume as discussed above in regards to the Phillips measurement cell. However, the Phillips design is not conducive to integrated UV measurement in the manner presented by Kalonia, et. al., utilizing a UV beam perpendicular to both the laser beam and the 90° scattering vector. For one thing the round fluid cavity of the Phillips cell would deflect the UV beam in ways that would make it difficult to control and correct. Additionally, the diameter of a reasonably-sized fluid cavity, e.g. 1.2 mm, would generally be too short a UV absorption path for reliable measurements. The simplest solution to improve sensitivity of the UV measurement would be to increase the bore diameter of the cell, however this would also increase the sample volume and hence be undesirable.

In the integrated cell proposed by Kolonia, the UV beam generally would be directed perpendicular to the generally horizontal plane of the MALS detectors. An integrated cell design has the advantage of simplicity in that there is only a single cell in which measurements are made, and the UV measurements will not disrupt the MALS measurements. The system as proposed by Kolonia requires that the UV source or UV detector be located under the flow cell, complicating the installation and constraining the overall system. If the UV beam is in the plane of the detectors, then either it is centered with respect to the flow cell bore and displaces the 90° MALS detector, or the UV beam is displaced laterally along the bore and away from the 90° detector. The former instance is undesirable as the light scattering detector at 90° is of central importance to MALS measurements. The latter instance adds a degree of band broadening into the measurement, although it is small relative to a system in which the measurement cells are separated by a length of tubing.

The present invention provides the advantages of an integrated MALS and concentration detection cell, while overcoming the disadvantages of current flow cell designs, both the Kalonia dual-detection cell and the Phillips MALS cell. This novel measurement cell system may utilize the cylindrical shape present in the Phillips cell design, which achieves significantly reduced stray light and permits the detection of light scattered at very small angles within the scattering plane. The cylindrical shape of the Phillips cell may be further modified in the manner presented by Trainoff in U.S. Pat. No. 7,982,875, issued Jul. 19, 2011, "Improved method and apparatus for measuring the scattered light signals from a liquid sample," incorporated herein by reference, wherein the cylindrical shape is further modified such that the lateral face of the cell is shaped such that it operates as a vertical lens as well. The present invention, however, also enables the simultaneous measurement of UV absorption at or near the same volume as that of the MALS detection volume. The present invention, in its different embodiments, overcomes the deleterious issues associated with the short path length of the Kalonia cell by either enabling multiple passes through the fluid in one embodiment, or, in another embodiment, directing the UV beam parallel to the MALS beam. The various embodiments of the present invention allow, for the first time, high quality measurement of both MALS and UV absorption at the same scattering volume.

Figure 3:
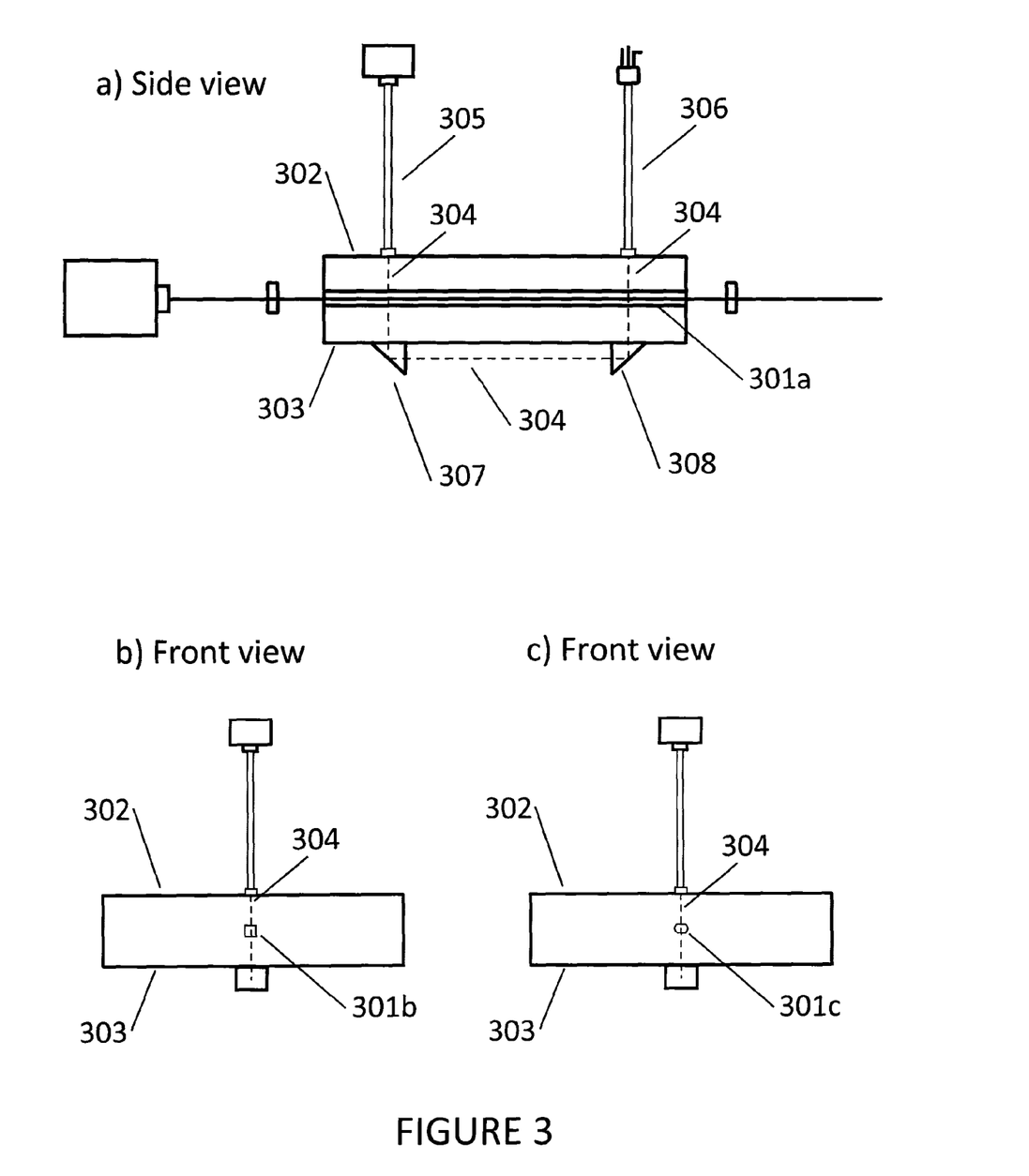
FIG. 3 shows a) one embodiment of the present invention with an integrated MALS/UV flow cell permitting passage of the UV beam through the central channel perpendicular to the MALS beam, b) a front view of the cell element showing one possible shape of the central channel, and c) a front view of the cell element showing another possible shape of the central channel. MALS detectors are not shown

One embodiment of the present invention is depicted in FIG. 3. This embodiment makes use of the basic design of the Phillip's cell, with the notable distinction that the central cavity 301 through which the fluid flows is of square or rectangular cross section, as also shown in front view as 301b in FIG. 3b. While the square or rectangular cross section is the simplest to describe, it should be noted that other shapes are also possible. In particular, one embodiment of the invention comprises a cell as shown in a front view in FIG. 3c comprising a central cavity 301c which is circular in cross section, except that the surfaces through which the UV radiation may be directed to pass are flattened along the length of the bore such that they are parallel to the surface or surfaces of the cell 302 and/or 303 through which the UV beam 304 will pass. Alternatively, at least at regions of the bore where UV radiation will be directed will be so flattened. One advantage of this novel cell system is that the UV beam 304 may enter and exit the cell at the same planar surface such as the top 302 or the bottom 304 of the cell, simplifying system design. Accordingly the UV beam 304 may be introduced from a distant source by means of an optical fiber 305, and the transmitted beam may be conducted to a distant detector by means of an optical fiber 306, with minimal disruption to the overall configuration of the cell and detector read head. Here the UV beam occupies essentially the same volume as is detected by the MALS detectors. The UV beam 304 is directed such that it is perpendicular to the opposite, parallel flat faces of the cavity 301. After emerging from the cell structure, the beam is then directed by means of a UV-grade fused silica Porro prism or mirror 307 such that it traverses a distance, generally parallel to the bore 301, before being redirected by means of another prism or mirror 308 to traverse the measurement bore a second time, effectively doubling the path length the UV beam has traveled through the sample. In another embodiment of the invention the coupled mirrors/prisms may be replaced by a single UV-grade fused silica dove prism. Alternately, properly placed optical fibers could act to collect the UV beam as it passes out of the cell structure, and redirect it for a subsequent pass there through. It should be noted that optical windows are depicted as separate elements in FIG. 3, however the present invention should not be considered as limited to having windows as separate elements from the flow cell. One variation on the embodiment depicted in FIG. 3, and relevant to most other embodiments, would include windows as part of the measurement cell itself, for example by introducing the fluid sample through an inlet bore perpendicular to the central cavity, and allowing the sample to exit through a similarly placed exit bore on the other side of the cell; thus the central chamber would not span the entire length of the diameter of the cell.

Figure 4:
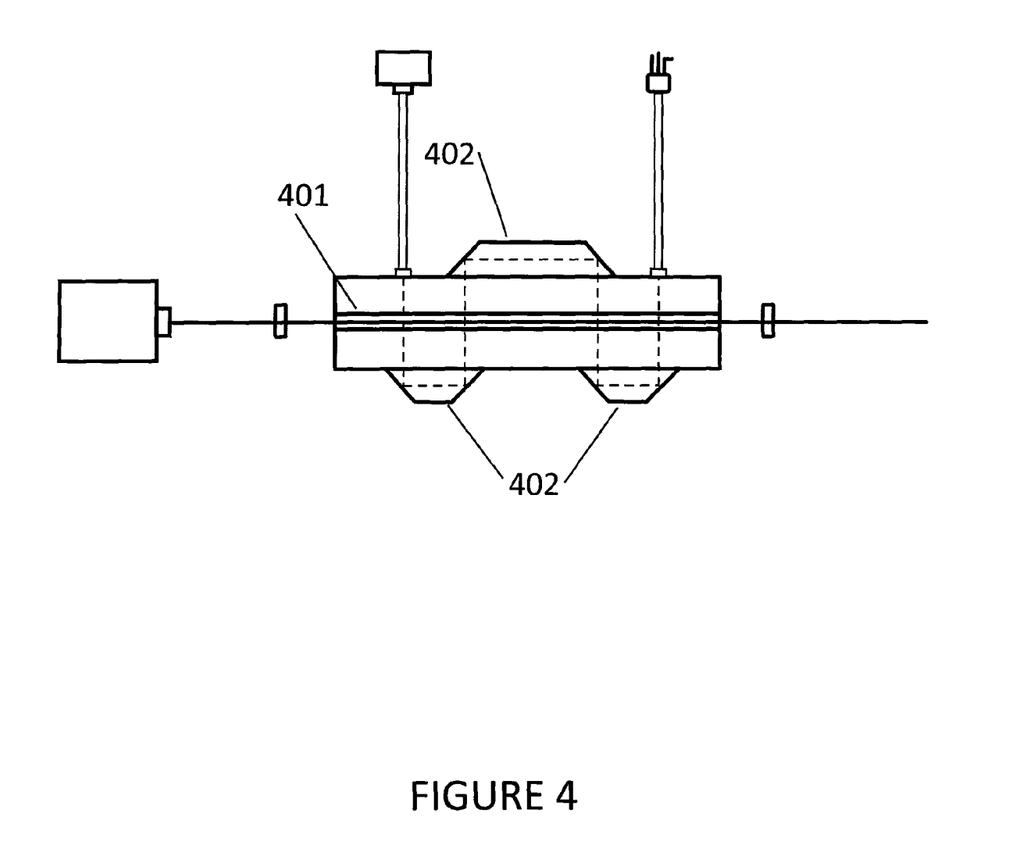
FIG. 4 illustrates an embodiment of the invention wherein the UV beam makes several passes through the central channel. MALS detectors are not shown.

As depicted in FIG. 4, multiple dove prisms or mirror sets may be utilized to enable even more passes through the flow cell measurement volume. Particular care may be taken to traverse the central cavity 401 multiple times within the MALS scattering volume, defined by the location of the MALS detectors, enabling the simultaneous measurement of UV absorption and MALS. This feature permits passing the UV beam through the glass-fluid interface multiple times with minimal distortion in order to achieve a relatively long effective absorption path length, increasing sensitivity. Simple design changes can introduce 2, 4, 6, 8 . . . etc. passes through the sample in order to address samples with higher or lower concentration ranges. The total path length traversed by the UV beam through the cell is then calculated to be two times the bore height times the number of round trips through the central cavity. This path length is then used in the calculation of the concentration value of the sample passing through the flow cell according to Eq. 1. The UV beam may be coupled initially to the flow cell by means of an optical fiber such as those produced by Ocean Optics (Dunedin, Fla.) or else a UV lamp may be placed in proximity with appropriate mirrors, lenses and apertures as is known in the art to produce a small, collimated beam. Similarly, the transmitted beam may be coupled to a remote detector via optical fiber or coupled to a detector in close proximity by means of mirrors and lenses as is known in the art.

While the prisms and/or mirrors are shown in FIGS. 3 and 4 as being placed on or near the surfaces of the cell, another embodiment of the present invention would integrate the UV beam driving means into the cell structure itself. It should also be noted that there is no limitation that the UV source and detection element exist on the same side of the cell. It may well be that an odd number of traversals through the measurement volume is desired, and thus the detector could be located on the opposite side of the cell as the source. Further multiple detectors could be designed into an instrument, with the UV beam directing elements aligned so as to direct the UV beam to any one, or indeed, any number of the detectors. For example, a partially silvered mirror might direct the a portion of the UV beam to a detector located above the cell, while directing the remaining beam to make another pass, or multiple further passes, through the cell to another UV detector.

Figure 5:
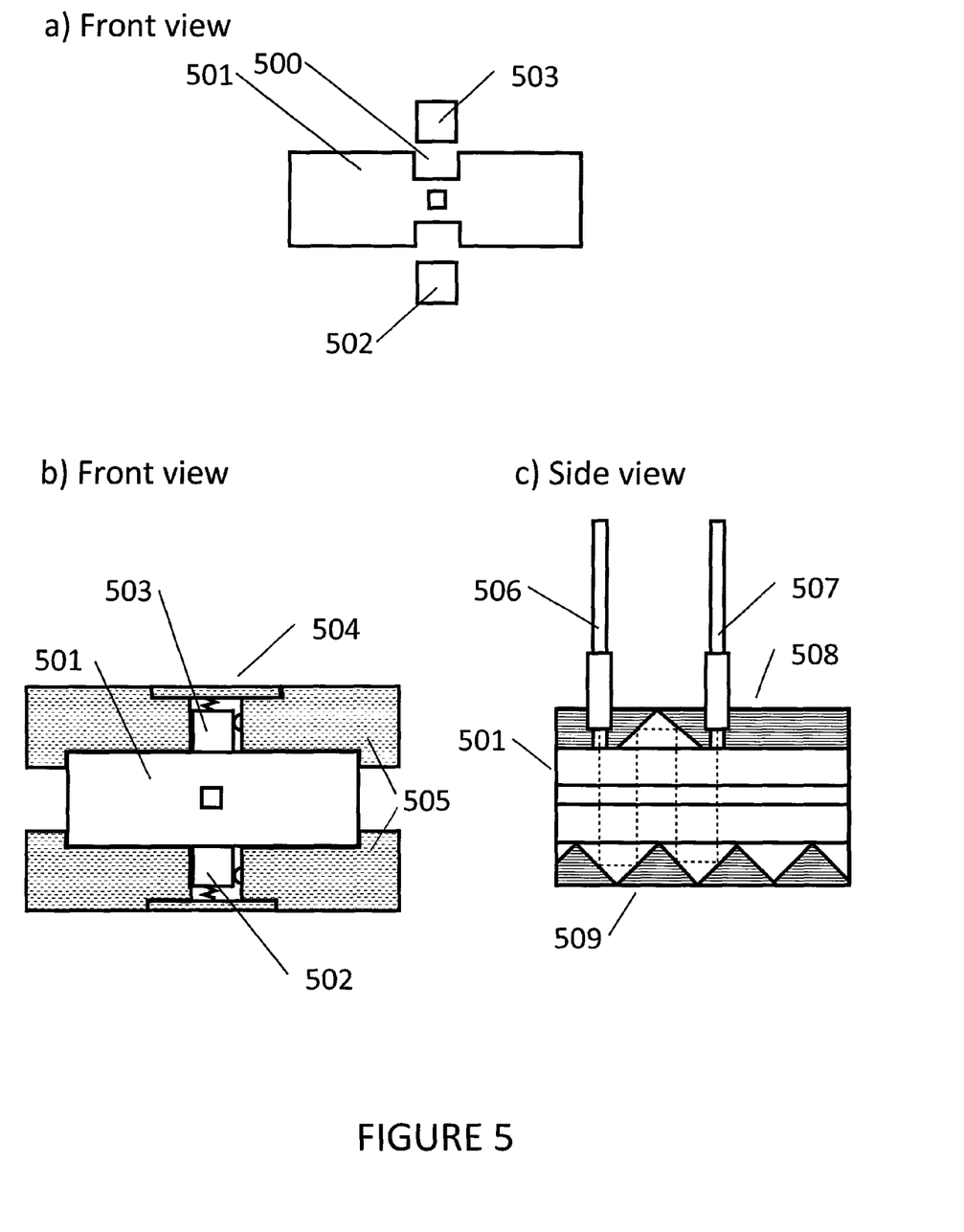
FIG. 5 illustrates embodiments of the invention wherein interchangeable top and bottom optical elements are used to direct the UV beam to make multiple passes through the central channel.

It is important to note that the desired sensitivity of the UV measurement will vary greatly depending on the concentration of the sample injected into the flow cell. As such, it is advantageous to enable the user to vary the number of passes the UV beam makes through the cell without the need to replace the cell or dramatically realign the optics of the combined light scattering/UV measurement instrument. Accordingly the inventive apparatus presented herein may include the use of interchangeable drop-in compartmentalized optical elements placed into the cell manifold, or into the cell body itself. Several such embodiments are shown in FIG. 5. These embodiments allow the user to vary the number of passes the UV beam makes through the central channel. These compartmentalized optical elements may contain the aforementioned Porro prisms or mirrors, or other beam directing means such as optical fibers. These elements 502 and 503 may be placed into a channel 500 within the cell manifold 505 or placed within the cell structure itself 501, and be pre aligned by means of bosses, springs, ball plungers, o-rings, grommets, spring washers, gaskets, or other alignment mechanisms and may held into place by a retainer 504, bosses, set screws, or other retaining means, or may be adhered to or within the cell structure itself. Thus several sets of these interchangeable optical elements 502 and 503 allow the user to select the number of passes the UV beam will make through the cell. These interchangeable components may also be used to select the region of the flow cell which is traversed by the UV beam. FIG. 5c shows a configuration whereby optical directing components 508 and 509 may be used to vary the total path length of the UV beam through the cell as well as well as the location through which the beam passes. In this embodiment it may be particularly advantageous to use optical fibers 506 and 507 to direct the UV beam to and from the cell structure. In the particular example shown in FIG. 5c, the use of a "universal" optical component 509 beneath the cell structure 501 can operate to redirect the UV beam 503 multiple times. The corresponding optical structure 508 utilized above the cell may be selected such that the desired number of passes is made through the cell without the need to realign the UV source if the fibers are used as shown. In the example shown here, four passes are made through the central channel within the first half of the cell. However, without the need to remove the bottom optical component 509 or the cell manifold from the instrument itself, the top optical component could be replaced, for example, by another with properly aligned optical directing elements contained therein, and appropriate receptacles for the optical fibers 506 and 507 to allow two, six or more passes through the cell. In addition other sections along the central channel could be measured by selection of an appropriately placed top optical directing component 508.

Figure 6:
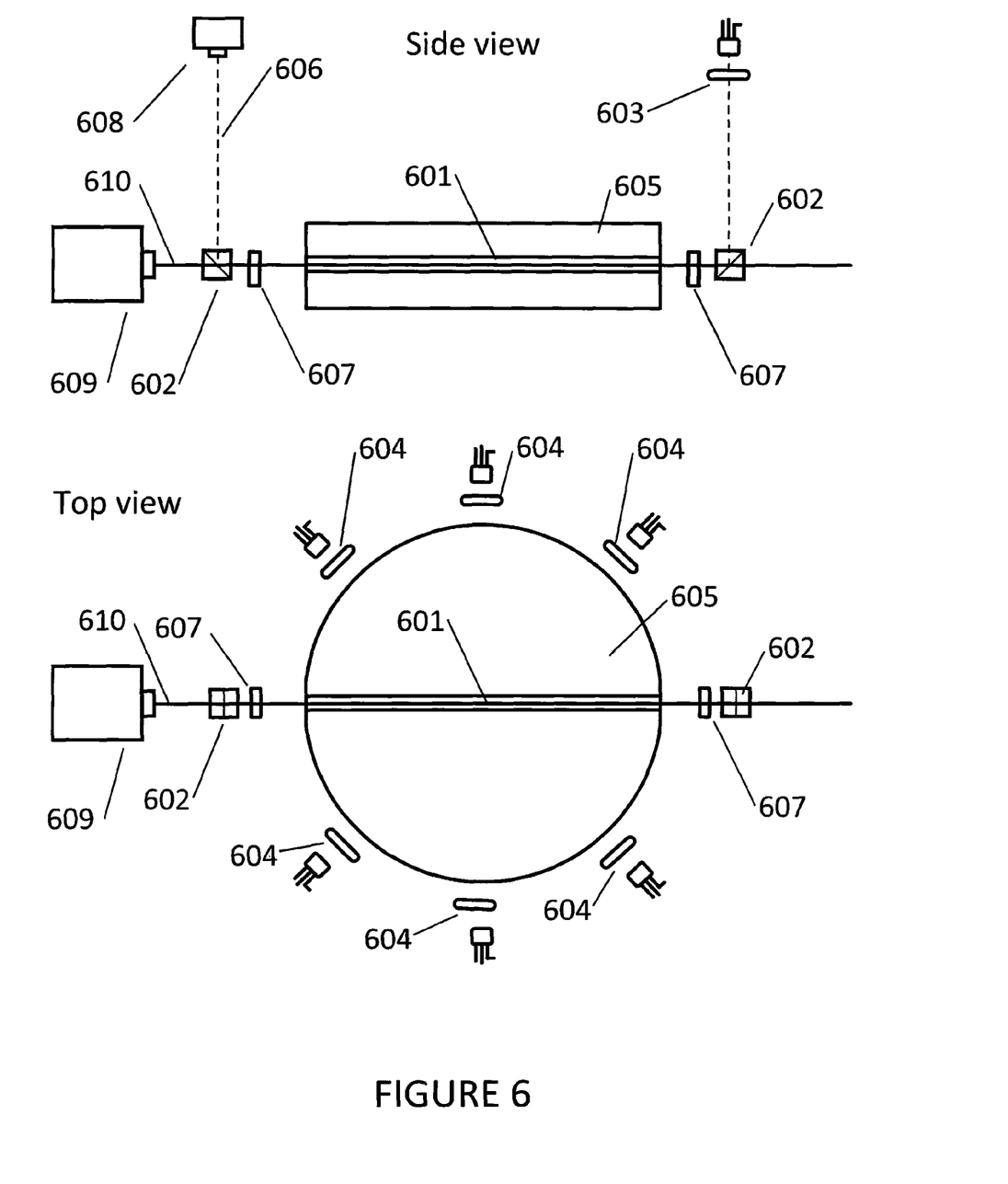
FIG. 6 shows side and top views of an embodiment of the invention wherein the UV light is transmitted through the cell parallel to the MALS beam. MALS detectors and associated filters are not shown in the side view.

Another embodiment of the present invention is depicted in FIG. 6. In this embodiment, the UV light source 608 emits UV beam 606 which is coupled into the cell structure 605 by means of a dichromic mirror or cube beam splitter 602 before passing through an optical window 607 and along the central bore 601 of the cell structure 605. After the UV beam has traversed the central bore 601 it passes through another optical window 607 and is directed by means of another dichromatic mirror or beam splitter to 602 to the UV detector 603. The light scattering source 609 emits a light scattering beam 610 which passes through the dichromatic mirror or beam splitter 602 and window 607 without significant deviation along its path. Light scattering detectors 604 positioned circumferentially around the cell structure 605 detect light scattered from the beam by the solution. In this embodiment, it is not necessary, nor particularly desirable that the central cavity 601 have a square cross section. Also, it is possible that the two beam sources might be switched, with the UV beam directed without significant deviation through the cell, while the light scattering beam's course is directed through the central bore by the dichromatic mirror or beam splitter 602. Furthermore, in order to increase sensitivity of the detectors, light from the MALS source could be obstructed from reaching the UV detector, and light from the UV source could be obstructed from reaching the MALS detectors. Since the MALS light source is typically a laser of a wavelength in the visible or near infrared range, one way of achieving this obstruction is to place bandpass filters in the detector optical paths. For example, assume that the MALS laser is of wavelength 658 nm and the UV beam of wavelength 280 nm, as is common in such instruments. A shortpass filter 603 placed in the UV detection path, which absorbs light over 400 nm but passes light under 400 nm, will effectively block laser light from reaching the UV detector. Conversely, a longpass filter 604 placed in the MALS detection path, which absorbs light under 400 nm but transmits light over 400 nm, will effectively block UV light from reaching the MALS detectors. Other filters besides longpass and shortpass may be used, e.g. notch filters that block or transmit narrow wavelength ranges. Other methods of selecting radiation from a particular light source are described later in the disclosure.

Figure 7:
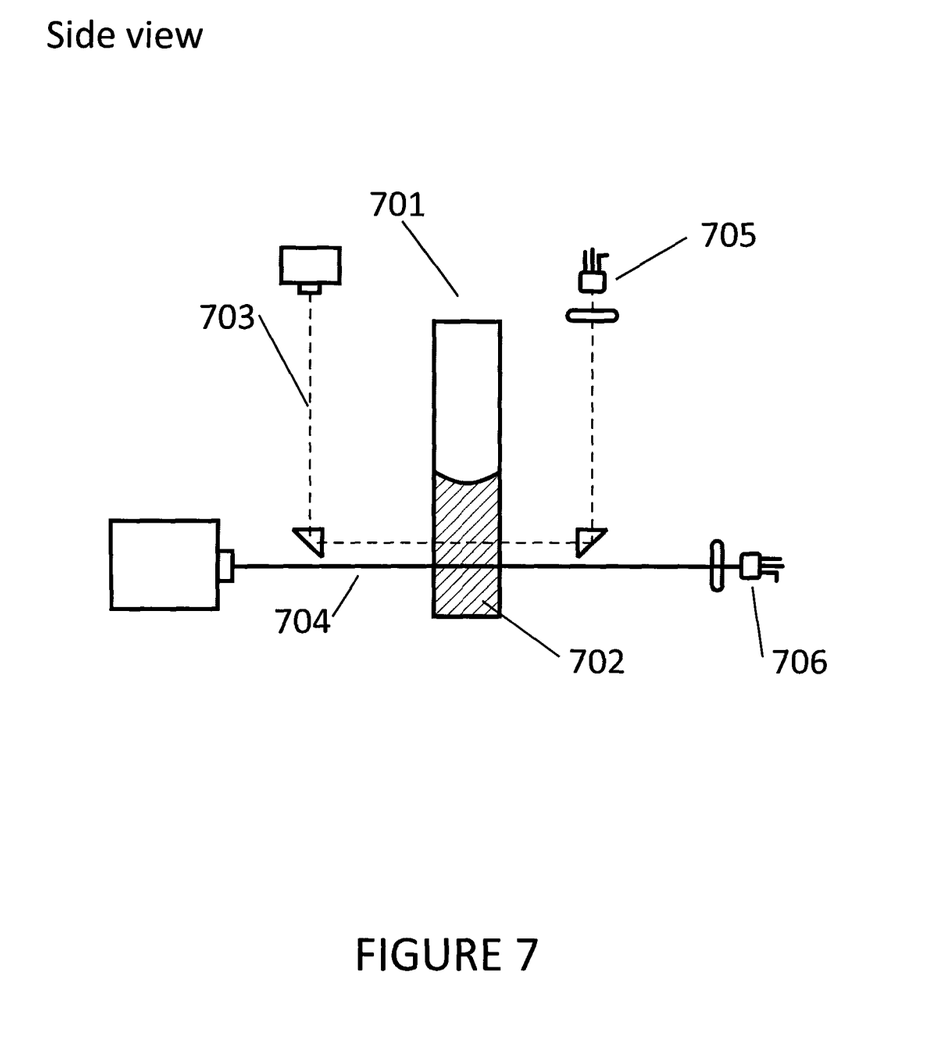
FIG. 7 shows a side view of an embodiment of the invention as it may be practiced in batch mode with a cuvette.
Figure 8:
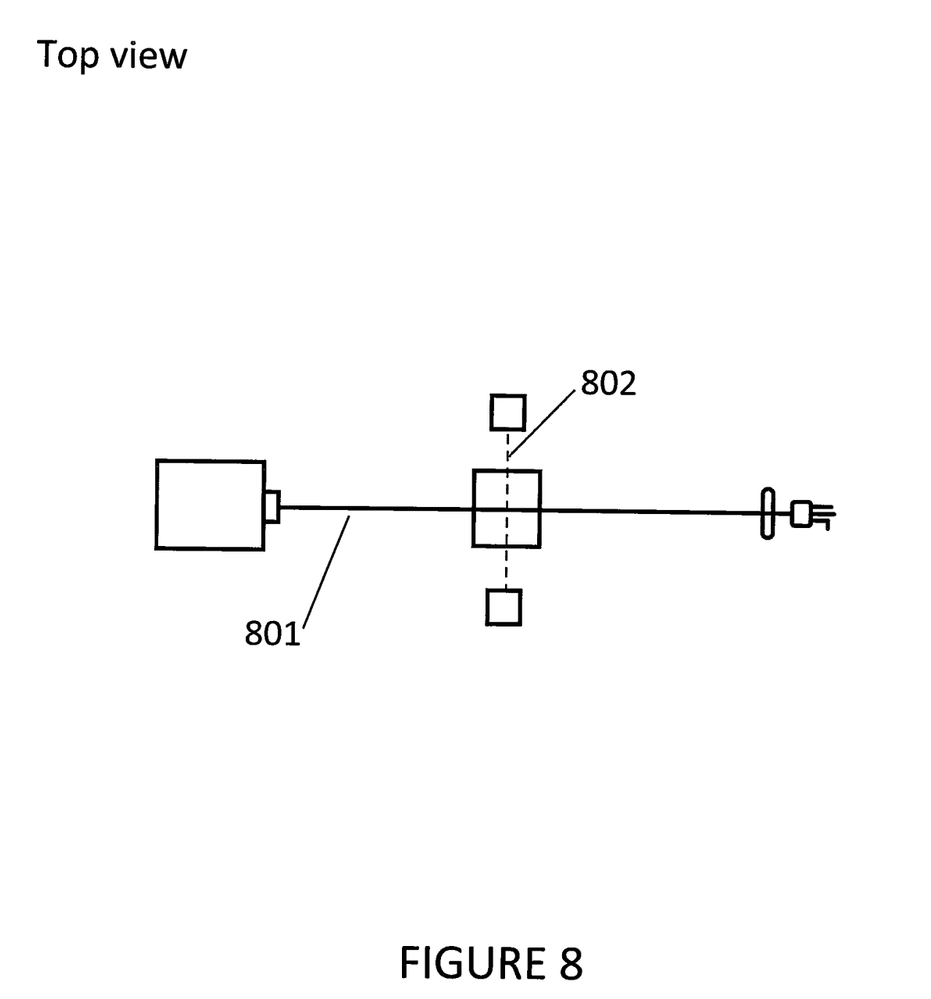
FIG. 8 shows a top view of an alternative embodiment of the invention practiced in batch mode wherein the UV and MALS beams are directed perpendicular to each other.

A further embodiment of the present inventive integrated MALS/UV cell system, as depicted in FIG. 7, enables the detection of light scattering and UV absorbance simultaneously within a cuvette 701 running in batch mode. In a similar system to that disclosed above, a liquot of the sample 702 to be measured is introduced into the cuvette 701 and the UV beam 703 passes above or beneath the MALS beam 704 with these beams parallel to each other and directed to the corresponding UV detector 705 or MALS beam dump 706. MALS detectors (not shown in FIG. 7) may be positioned at 90° from the MALS beam, and detectors at other angles may be additionally positioned around the cuvette. Alternatively, dichromic cube beam splitters could be used such that the paths of the UV and MALS beams overlap as discussed in the embodiment disclosed in the flow cell embodiment represented in FIG. 6. In yet another embodiment of the cuvette implementation of the present invention, the MALS and UV beams, 801 and 802 respectively, may be perpendicular, or near perpendicular, to each other, as shown in FIG. 8. In this implementation, the beams would generally operate in different planes, therefore, never actually crossing. This configuration facilitates the placement of the UV detector along with a 90° MALS detector, which would not be possible if the beams did not occupy separate planes.

Figure 9:
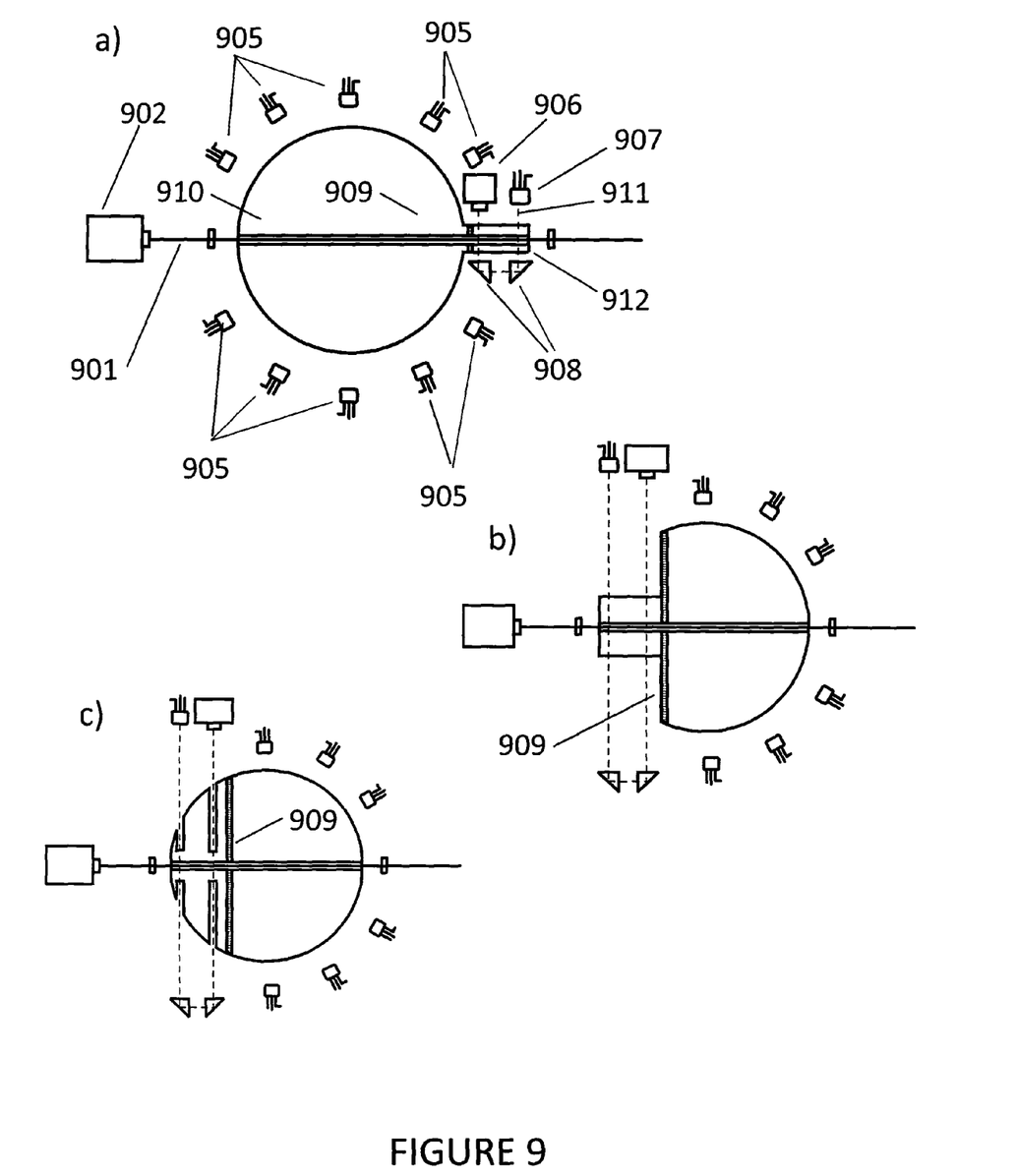
FIG. 9 shows three possible configurations of a cell structure to measure light scattering either upstream or downstream from the UV absorption measurement volume with an absorbing material isolating the two measurement volumes.

Still another embodiment of the invention is shown in FIG. 9. In this embodiment, the UV measurement is made at a short distance from the LS measurement, but in closer proximity than in most systems presently used in the art. In this embodiment, the light scattering detectors 905 may still be aligned to measure light scattered from the light scattering beam 901 which is produced by the light scattering source 902 that occurs near the center of the cylindrical area of the cell structure 910, but the UV detection, comprising a UV source 906 and UV detector 907, occurs either slightly before or slightly after the light scattering volume as the flow proceeds through the cell, but may be within the plane defined by the light scattering detectors 905. This may be accomplished by the use of a novel shape for the cell. In particular, a cell may have a rectangular prism shape 912 appended to the right circular cylindrical shape along the flow path, as shown in FIG. 9a, or may have a section of the cylindrical shape 910 cut therefrom to provide flat surfaces through which the UV beam 911 may enter and exit the cell as shown in FIG. 9b. Similar to the embodiments described previously, optical elements 908 are employed to direct the beam to pass through the cell multiple times. Other geometries for the cell structure are also possible, for example, maintaining the cylindrical shape of the cell throughout, but cutting channels into the cell structure to provide flat surfaces through which the beam may pass as shown in FIG. 9c. In order to improve the overall optics of the such a cell structure, a plane of optically absorbing material 909 may be incorporated into the cell structure such that the absorbing material prevents unwanted scattering, reflection or other optical interference from the various interfaces. Such an optically absorbing material may be simply a plane of blackened glass or other material incorporated into the cell structure, or a material selected to specifically absorb light at the wavelength of either or both of the light sources. While analyzing the UV signal upstream or downstream from the light scattering signal may be suboptimal in some respects, this embodiment nonetheless provides improvement in overall band broadening over conventional designs. There are many orientations which the cell structure geometry may take, including the light scattering detection occurring earlier along the flow stream than the UV detection as shown in FIG. 9a, or later along the flow stream as shown in FIG. 9b.

Figure 10:
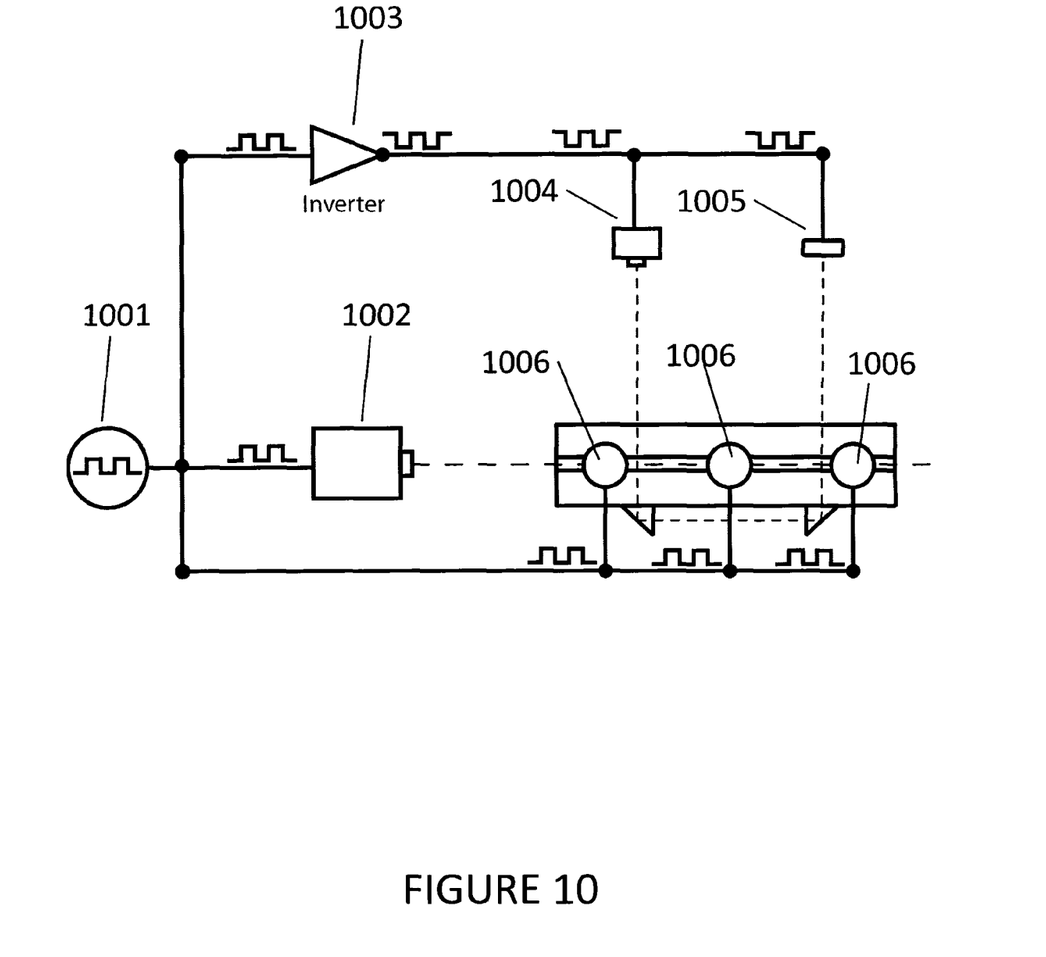
FIG. 10 is a graphical representation of an electrical modulation system whereby current is supplied to the two light sources and respective detectors.

As briefly discussed above, another means by which the MALS and UV signals may be kept from interfering with each other and causing the detectors to confuse light scattered by the non-corresponding source, the MALS and UV sources may be turned on and off in anti-phase and the corresponding detectors turned on and off synchronously, either by electrical or mechanical blockage means, so as to eliminate the transmission of light from one source while light from the other source is being measured. A method for electrical blockage may include turning on and off the laser in succession by, for example, imposing a square or sine wave as the power sources, as illustrated in FIG. 10. Power source 1001 produces a modulated current which powers the light scattering source 1002 and the light scattering detectors 1006 synchronously. Current from the power source 1001 may be split and passed through an electrical inverter 1003 prior to providing operating power to the UV source 1004 and UV detector or detectors 1005. Alternate methods for providing power to the light sources and corresponding detectors in anti-phase are also possible. For example the use at two separate power sources producing current in anti-phase. Additionally, rather than powering the detectors directly, the alternating power source may power, rather, the signal amplification means or independent analog-to-digital converters associated with each set of detectors, thus effectively modulating the signals by transmitting data therefrom only when the power to the converter or amplifier is in the on state. Mechanical blockage may be achieved by using a chopper, similar to a rotating fan blade, as is well known in the art, which blocks the beam at one or more points in its rotation and allows the beam to pass through at alternating intervals. Alternatively, the MALS laser source may be modulated at a specific frequency, and the MALS and UV detector signals processed electronically to accept or reject signals at the frequency of the modulated component as appropriate.

While the descriptions of the above referenced embodiments disclose the use of light scattering detectors in addition to UV absorption detectors, it should be noted that any of the detectors may also measure fluorescence of the sample due to exposure to a particular wavelength of light. Multiangle light scattering measurements are often made at wavelengths specifically chosen to be unlikely to cause fluorescence of the sample which can interfere with light scattering detection and cause erroneous results. However, the present invention can actually make use of fluorescence as a means of concentration detection while still permitting light scattering measurements at wavelengths unlikely to cause fluorescence. This can be accomplished in an embodiment of the invention wherein one or more of the detectors directed to receive a signal from the light scattering sample volume is selected to act as a fluorescence detector. This may be accomplished, for example, in the embodiment shown in FIG. 5 by the removal of one of the filter elements 504 which had been selected to reject light from a wavelength much different from that of the light scattering source. It is the implementation of this novel invention wherein the sample is exposed to light of at least two wavelengths that enable the simultaneous, or near simultaneous, measurement of light scattering fluorescence and absorption. This fluorescence measurement enabling apparatus is not limited to the embodiment shown in FIG. 5, but may be equally useful to most of the embodiments described herein, so long as at least one detector is able to measure any fluorescence.

There are many embodiments of our invention that will be obvious to those skilled in the arts of measurement optics that are but simple variations of the basic invention herein disclosed that do not depart from the fundamental elements that we have listed for their practice; all such variations are but obvious implementations of the invention described hereinbefore and are included by reference to our claims, which follow.

The invention claimed is:

1. An apparatus for measuring physical properties of a suspension of particles in a liquid sample comprising
   A) a flow through measurement cell comprising a bore into which said liquid sample is injected through an injection port, and out of which said liquid sample passes through an outflow port;
   B) a scattering light source that emits a scattering light beam directed to pass along the bore of said measurement cell, illuminating said liquid sample;
   C) one or more light scattering detectors positioned to measure light scattered from said scattering light beam by said particles in said liquid sample;
   D) a UV light source that emits a UV light beam directed to pass through the bore of said measurement cell illuminating said liquid sample, wherein the wavelength of said UV light beam is different from the wavelength of said scattering light beam;
   E) optical means directing said UV light beam to pass through said bore one or more additional times; and
   F) a UV detector positioned to measure light transmitted through said liquid sample by said UV light beam after said transmitted UV light beam has passed through said measurement cell a plurality of times.

2. The apparatus of claim 1 wherein the surfaces of said measurement cell through which said UV light beam is directed to pass are parallel to each other.

3. The apparatus of claim 2 wherein the cross section of said bore is rectangular.

4. The apparatus of claim 2 wherein the cross section of said bore is circular except at and near the points where said UV light beam is directed to pass.

5. The apparatus of claim 1 wherein said optical means to direct said UV light beam to pass through said bore one or more additional times are integrated into said measurement cell.

6. The apparatus of claim 1 further comprising one or more optical filters placed between said measurement cell and one or more of said scattering detectors, said optical filters selected to inhibit the passage of light at the wavelength of said UV light source.

7. The apparatus of claim 6 wherein one of said light scattering detectors does not have said optical filter placed between said detector and the measurement cell, and said unfiltered light scattering detector operates as a fluorescence detector.

8. The apparatus of claim 1 further comprising an optical filter placed between said measurement cell and said UV detector, said optical filter chosen to inhibit the passage of light at the wavelength of said scattering light source.

9. The apparatus of claim 1 wherein the measurement volume of said scattering detectors is located at a different point along said bore from the measurement volume of said UV detector, and said measurement cell further comprises a plane of optically absorbent material located between said measurement volumes.

10. The apparatus of claim 9 wherein said bore is of circular cross section at said measurement volume of said scattering detectors and is of rectangular cross section at said measurement volume of said UV detector.

11. The apparatus of claim 1 wherein said UV light source is a lamp and said UV detector is a spectrophotometer.

12. The apparatus of claim 1 further comprising a means for modulating the light scattering and UV light beam wherein said modulating means comprises a power source which provides power alternately to said scattering light source and said UV light source and/or said scattering detectors and said UV detector.

13. The apparatus of claim 1 further comprising a means for modulating the light scattering and UV light beam wherein said modulating means comprises mechanical choppers to interrupt said beams in anti-phase.

14. The apparatus of claim 1 wherein said optical means to direct said UV light beam comprises
   a. angular elements etched into the bottom surface of said measurement cell at appropriate angles; and
   b. a reflective film adhered to said bottom surface of said measurement cell, said film selected to reflect light at the wavelength of said UV light beam;

wherein said appropriate angles are chosen such that said UV beam, after passing through said central bore is reflected by one said etched angular elements to another angular element which directs said UV beam back through said central bore.

15. A method for measuring physical properties of a liquid suspension of particles comprising the steps of
   A) injecting a fluid containing said liquid suspension of particles into a transparent flow through measurement cell;
   B) directing a scattering light beam from a scattering light source through said measurement cell illuminating said particles;
   C) detecting light scattered from said scattering light beam by said particles;
   D) directing a UV light beam of a wavelength different from that of said scattering beam to pass through said measurement cell illuminating said particles;
   E) directing said UV light beam to pass through said measurement cell one or more additional times; and
   F) detecting light transmitted by said UV light beam after having passed through said measurement cell a plurality of times.

* * * * *